United States Patent [19]

Cook

[11] Patent Number: 4,774,941
[45] Date of Patent: Oct. 4, 1988

[54] RESUSCITATOR BAG

[75] Inventor: Wallace F. Cook, Yorba Linda, Calif.

[73] Assignee: Intertech Resources Inc., Bannockburn, Ill.

[21] Appl. No.: 941,573

[22] Filed: Dec. 11, 1986

Related U.S. Application Data

[63] Continuation of Ser. No. 766,673, Aug. 16, 1985, abandoned, which is a continuation of Ser. No. 491,572, May 4, 1983, abandoned.

[51] Int. Cl.⁴ ............................................. A62B 7/04
[52] U.S. Cl. ........................... 128/205.13; 128/205.24; 137/102; 137/908
[58] Field of Search ...................... 128/203.11, 203.28, 128/205.11, 205.13, 205.17, 205.24, 911; 137/102, 512.4, DIG. 9

[56] References Cited

U.S. PATENT DOCUMENTS

| | | | |
|---|---|---|---|
| Re. 24,193 | 8/1956 | Emerson | 128/205.24 |
| Re. 28,486 | 7/1975 | Ruben | 128/205.13 |
| 2,399,643 | 5/1946 | Kreiselman | 128/205.24 |
| 2,428,451 | 10/1947 | Emerson | 128/205.24 |
| 2,737,177 | 3/1956 | Anklin | 128/205.24 |
| 2,823,667 | 2/1958 | Raiche | 128/205.24 |
| 3,009,459 | 11/1961 | Ruben | 128/205.13 |
| 3,046,978 | 7/1962 | Lea | 128/205.13 |
| 3,086,542 | 4/1963 | Mosler | 137/102 |
| 3,093,153 | 6/1963 | Horowitz | 137/102 |
| 3,196,866 | 7/1965 | Adams | 128/205.24 |
| 3,262,446 | 7/1966 | Stoner | 128/205.13 |
| 3,356,100 | 12/1967 | Seeler | 128/205.13 |
| 3,363,833 | 1/1968 | Laevdal | 128/205.13 |
| 3,515,163 | 6/1970 | Freeman | 137/102 |
| 3,519,012 | 7/1970 | Van Patten | 137/102 |
| 3,556,122 | 4/1971 | Laevdal | 137/102 |
| 3,650,268 | 3/1972 | Ruben | 128/205.13 |
| 3,672,366 | 6/1972 | Barchell et al. | 137/102 |
| 3,726,274 | 4/1973 | Bird et al. | 128/205.12 |
| 3,739,801 | 6/1973 | Rudolph | 137/102 |
| 3,795,257 | 3/1974 | Fabish et al. | 137/102 |
| 3,799,185 | 3/1974 | Milnes et al. | 137/102 |
| 3,882,860 | 5/1975 | Frimberger | 137/DIG. 9 |
| 3,902,516 | 9/1975 | Rudolph | 137/102 |
| 3,942,547 | 3/1976 | Pfitzne | 137/102 |
| 3,978,878 | 9/1976 | Rudolph | 137/102 |
| 4,037,595 | 7/1977 | Elam | 128/205.11 |
| 4,071,025 | 1/1978 | Kohnke | 128/205.13 |
| 4,077,404 | 3/1978 | Elam | 128/205.13 |
| 4,084,606 | 4/1978 | Mittleman | 137/102 |
| 4,088,131 | 5/1978 | Elam et al. | 128/205.13 |
| 4,121,580 | 10/1978 | Fabish | 128/205.13 |
| 4,167,184 | 9/1979 | Kohuke | 128/205.13 |
| 4,190,045 | 2/1980 | Bartels | 128/205.24 |
| 4,239,038 | 12/1980 | Holmes | 128/205.13 |
| 4,374,521 | 2/1983 | Nelson et al. | 128/205.13 |
| 4,622,964 | 11/1986 | Flynn | 128/205.24 |

FOREIGN PATENT DOCUMENTS

| | | | |
|---|---|---|---|
| 745432 | 11/1966 | Canada | 128/205.24 |
| 0139363 | 5/1985 | European Pat. Off. | 128/205.13 |
| 2320118 | 4/1977 | France | 128/205.24 |
| 56058 | 5/1967 | German Democratic Rep. | 128/205.24 |
| 185702 | 8/1966 | U.S.S.R. | 128/205.24 |
| 748363 | 5/1956 | United Kingdom | 137/102 |
| 750152 | 6/1956 | United Kingdom | 137/102 |
| 791005 | 2/1958 | United Kingdom | 137/102 |
| 802217 | 10/1958 | United Kingdom | 137/102 |
| 843586 | 8/1960 | United Kingdom | 128/205.13 |
| 875790 | 8/1961 | United Kingdom | 128/205.24 |
| 1006984 | 10/1965 | United Kingdom | 128/205.13 |
| 1481246 | 7/1977 | United Kingdom | 137/102 |
| 2015349 | 9/1979 | United Kingdom | 128/205.13 |

OTHER PUBLICATIONS

AGA Medical, "AGA Revivator", 6 pages, (date unknown).
Steven P., McPhersen, "Respiratory Therapy Equipment", (C. V. Mosely Co. St. Louis, 1977) pp. 141–157.
Puritan Medical Products, "PMR 2 Puritan Manual Resuscitator", 1980, pp. 1–8.
Laerdal Medical Corporation, "Laerdal Resuscitators", 2 pages (date unknown).
Narco Air Shields, "MS-30", 1 page, 1980.

Primary Examiner—Edward M. Coven
Assistant Examiner—K. M. Reichle
Attorney, Agent, or Firm—Marshall, O'Toole, Gerstein, Murray & Bicknell

[57] ABSTRACT

A resuscitation apparatus for use during medical procedures is disclosed. The device comprises a squeeze bag having a gas inlet and a gas outlet, and a specifically configured valve joined to the bag over the gas outlet. The valve housing includes a squeeze bag port in flow communication with the gas outlet opening, a patient port and an exhalation port. The valve disposed in the housing includes a portion for directing fluid from the squeeze bag through the patient port during inhalation or forced respiration and through the exhalation port during exhalation. Another portion of the valve closes off the exhalation port during inhalation or forced respiration such that fluid from the squeeze bag is directed to the patient.

6 Claims, No Drawings

RESUSCITATOR BAG

This application is a continuation, of application Ser. No. 766,673, filed 8-16-85, now abandoned, which is a continuation of application Ser. No. 491,572 filed May 4, 1983, now abandoned.

BACKGROUND OF THE INVENTION

1. Field of the Invention

This invention relates to the field of medical devices, and more particularly, to breathing equipment such as resuscitators.

2. Prior Art

Manual resuscitators using self-inflating bags are well recognized in the prior art. Such devices are often used during "cardio-pulmonary resuscitation", often times referred to as "CPR". During such procedure, it is necessary to supply the patient with large quantities of air or oxygen. In addition to forcing a volume of air to the patient, such devices must also take into account the fact that the patient may inhale or exhale under his or her own ability. As a result, resuscitation bags are usually comprised of three basic components; to wit: a mask, a specific directional control valve arrangement, and a squeezable bag.

The mask is used to form a seal about the patient's nose and mouth. As such, it is typically made of a soft, pliable material and is sufficiently flexible so as to contour to a wide variety of facial features. Typically, the body of the mask must be sufficiently rigid to allow uniform force to be applied so as to make the seal.

The directional control valve located adjacent the mask must allow air to be forced under pressure to the patient and should also permit the patient to exhale. In addition, the valve should allow the patient to breathe spontaneously by drawing air through the bag (not forced under pressure) and to exhale.

The bag is the means for supplying air under pressure to the patient. Such bags are well known in the art and generally include a one-way check valve at the end opposite the regulator valve so as to permit air to flow in one direction only into the bag. Generally, such bags should be compliant and permit 40 cycles per minute operation while delivering a minimum of 500 cc. of air per cycle at 100 cm. of water pressure.

While each of the elements discussed above are recognized by the prior art, heretofore the prior art has created resuscitation bags and masks which had various problems including complexity in design and/or operation, expense, and the like. These as well as other shortcomings have plagued this area of endeavor a substantial period of time. Examples of prior art bags and masks are shown in U.S. Pat. Nos. 3,363,833; 4,037,595; 4,121,580; and 3,556,122. The present invention addresses these problems and provides a disposable bag and valve construction which are straight forward in their design, but yet effective in their operation.

SUMMARY OF THE INVENTION

In the resuscitation apparatus of the present invention, a squeeze bag is provided which includes a first directional control valve housing joined to a first end of the bag. The first valve housing has a squeeze bag port, a patient port and an exhalation port. A first valve means is disposed in the first valve housing for controlling the flow of fluid to and from the patient. The first valve means comprises a one-way valve portion for directing fluid from the squeeze bag through the patient port during inhalation or forced respiration and through the exhalation port during exhalation, and a diaphragm portion for closing off the exhalation port during inhalation or forced respiration. A second check valve means is disposed on the squeeze bag for directing fluid into the squeeze bag.

The first valve means thus enables three operations to take place: (1) "forced respiration"; (2) "free exhalation"; and (3) "spontaneous breathing" through the bag. Regardless of whether there is forced respiration or spontaneous breathing by the patient, the apparatus of the present invention permits exhalation to take place.

Forced respiration is started with the pressurization of the bag. The first valve means seals the exhalation port. With the exhalation port closed off, air is forced to the patient through the patient port. The first valve means will remain in this position as long as the bag pressure is maintained greater than the atmospheric pressure. When bag pressure is removed, the first valve means will shift due to the patient lung pressure thereby opening the exhalation port for fluid flow from the patient. The patient is now free to exhale through the exhalation port.

Free exhalation is achieved by directing exhaled air out of the exhalation apparatus through the exhalation port. This is also achieved by the configuration of the first valve means. This configuration is maintained as long as there is exhalation pressure.

Spontaneous breathing is permitted as the first valve means enables the patient to easily draw air from the bag through the patient port. Because the first valve means in its static position seals off the exhalation port during free inhalation, the patient inhales the fluid which is in the bag. In this manner, control over the fluid directed to the patient can be achieved. This valve configuration is maintained as long as the patient is inhaling. When a patient stops inhaling and starts to exhale, the first valve means shifts to permit free exhalation.

The novel features which are believed to be characteristic of this invention, both as to its organization and method of operation, together with further objectives and advantages thereof will be better understood from the following description considered in connection with the accompanying drawings in which a presently preferred embodiment of the invention is illustrated by way of example. It is to be expressly understood, however, that the drawings are for the purpose of illustration and description only, and are not intended as definition of the limits of the invention.

BRIEF DESCRIPTION OF THE DRAWINGS

FIG. 1 is a perspective view showing the various elements of the resuscitation apparatus of the present invention.

FIG. 2 is a cut-away view of FIG. 1 taken along lines 2—2 and showing the operation of the first valve means of the present invention.

FIG. 3 is a cut-away view showing another operation of the first valve means of the present invention.

DETAILED DESCRIPTION OF THE INVENTION.

Referring first to FIG. 1, there is shown, as a presently preferred embodiment of the present invention, the bag and mask assembly 10. As one can see, assembly 10 is comprised of an elongated, generally flexible squeeze bag 12 such as is well known in the art. Typically, bag 12 is of a transparent or translucent plastic and can be readily deformed with hand pressure. Bag 12 includes a first end 14 defining a gas outlet opening and a second end 16 defining a gas inlet opening. A first valve housing 18 is joined to the bag 12 adjacent the first end 14 thereof. Housing 18 includes a first upper bulbous section and a depending lower section joined to bag 12. A second valve housing 20 is joined to the second end 16 of the bag 12. Conduit 22 is joined to the first valve housing 18 and enables a face mask 24 to be joined to the bag 12 in flow communication therewith. Face mask 24 is conventional and will not be described in detail herein.

Joined to the second valve housing 20 is a flexible hose or conduit 26 which may include tubing 28. Tubing 28 can be joined to an external gas source so as to regulate the type of gas being supplied to bag 12. In this manner, specific gases such as an enriched oxygen mixture and the like can be ultimately supplied to the patient as hereinbelow described in greater detail.

Referring now to FIGS. 2 and 3, one can see that valve housing 18 includes a first valve means comprising a flexible duck-billed diaphragm 30 held in position by retaining snap ring 34. Duck-billed diaphragm 30 is of one-piece construction comprised of a centrally located duck-billed portion 30a, an integral, generally flat concentric sealing ring portion 30b, and an outer, annular flexible convolute shuttle portion 32. Duck-billed portion 30a is disposed in valve housing 18 such that it preferably extends up into a first patient port 36. Extending generally perpendicular with respect to the axis of the patient port 36 is an exit port 38. Housing 18 also defines an open port 39 which surrounds the first end 14 of bag 12. Ports 36 and 39 are in flow communication with bag 12, while annular exit port 38 is in selective flow communication with the patient. The annular portion 32 extends beyond the plane defined by the end 36a of patient port 36, and into the annular exit port 38.

Referring now to valve housing 20, one can see that it encloses a second diaphragm valve 40 and a diaphragm body 42. Diaphragm 40 and body 42 define a one-way valve, such valves being well known in the art. In the present invention, fluid is permitted to flow into bag 12 through openings 45 only in the direction of arrows 100. Diaphragm 40 is preferably mounted on protrusion 44 centrally located on body 42 as it is also conventional in the art. A cap 46 circumferentially surrounds the body 42 and is disposed on the bag 12 adjacent the second end 16 thereof. Cap 46 has an oxygen inlet port 48 which permits fluid to readily flow into the bag 12, and a flow control orifice 52 as hereinbelow described in greater detail.

In the operation of assembly 10, as squeeze bag 12 is depressed, internal pressure causes the diaphragm 40 to press against diaphragm body 42 and thus closes off openings 100 and the second end 16 of the bag 12. Fluid within the bag 12 is therefore forced through the duck-billed valve portion 30a, port 36 and into mask 24. This is illustrated in FIG. 2. To prevent fluid from flowing out of exit port 38, the flexible diaphragm 30 abuts up against tubular extension or end 36a of port 36. More specifically, the generally flat concentric sealing ring 30b abuts against end 36a. In the preferred embodiment end 36a forms a beveled seat to insure proper sealing with ring 30b. This seals off exit port 38 with respect to the flow of fluid from the bag 12. The operation of squeezing the bag 12 to force a volume of air or other fluid to a patient is generally referred to as forced respiration. If desired, conduit 28 can be joined to a source of fluid such as oxygen or the like so as to create an oxygen rich mixture which can then be directed to the patient.

During the free exhalation function, air or other fluid would be exhaled by the patient and flows through the conduit 22 towards the bag 12. However, such pressure causes the duck-billed valve portion 30a to close and the sealing ring portion 30b of the flexible diaphragm 30 to move away from the end 36a of port 36. This is shown in FIG. 3. In this manner, the exit port 38 is now in flow communication with port 36 and the exhalate flows through the exit port 38 to the outside. This valve configuration is maintained as long as there is an exhalation pressure.

Should the patient exhibit spontaneous breathing, the first valve means of the present invention permits this to readily take place. When the patient draws air in without the bag 12 being squeezed, the vacuum created will insure the valve diaphragm 30 to be sealed against the end 36a of port 36 and the duck-billed portion 30a to open such as is described above with respect to force respiration. The vacuum also causes the valve diaphragm 40 to open and air to flow through the bag 12 to the patient. When the patient stops inhaling and starts exhaling, the diaphragm 30 shifts to allow free exhalation as described above.

When the squeeze bag 12 is squeezed and released, a vacuum is created thereby closing duck-billed portion 30a, and simultaneously opening check valve diaphragm 40. This enables fluid to be drawn into squeeze bag 12 through openings 45. During bag refill, valve diaphragm 30 is design to permit simultaneous patient exhalation. 2

Yet another unique feature of this invention is the use and placement of a disk-shaped flow controller 50 defining flow control orifice 52. Controller 50 is disposed in removable cap 46. This enables one to disconnect the flow controller 50 from bag 12 should unrestricted flow into bag 12 be desired. Controller 50 is designed to overcome a problem with prior art bag when oxygen is being used. In the prior art bag oxygen typically cannot be supplied fast enough. Thus during bag refill, a greater- than-desired amount of air is drawn into the bag diluting the oxygen. In the present invention, oxygen is fed into bag 12 through tubing 28. During bag refill, the flow of air is restricted by means of orifice 50 thus enabling more oxygen to flow into bag 12. In addition, during other operations of the bag 12, oxygen from tubing 28 flows back through orifice 52 and fills hose 26. During bag refill, hose 26 thus acts as a reservoir enabling yet additional oxygen to flow into bag 12.

Yet another feature of the present invention is that should end 16 of the bag 12 become occluded, the patient can still draw fluid through port 36. This is achieved as during inhalation with end 16 occluded, a vacuum is formed in bag 12 thus drawing diaphragm 30 and ring 30b into bag 12. When ring 30b disengages from end 36b of port 36, fluid can then be drawn into the apparatus through port 38, and directed to the patient.

While the presently preferred embodiment has been described above, it is apparent to one skilled in the art that other embodiments are also within the scope of the present invention. For example, diaphragm 30 can be held in place by sealing means other than ring 34 i.e. by bonding and the like. Housing 18 can also be made in 2-parts for retaining diaphragm 30 and for easy disassembly and cleaning. Duck-billed portion 30a can also be replaced with a flapper-type check valve joined to portion 30b. In addition, other elements can be easily joined to apparatus 10 such as PEEP equipment, because of the easy access to port 38. This invention, therefore, is not to be limited to the particular embodiment herein disclosed.

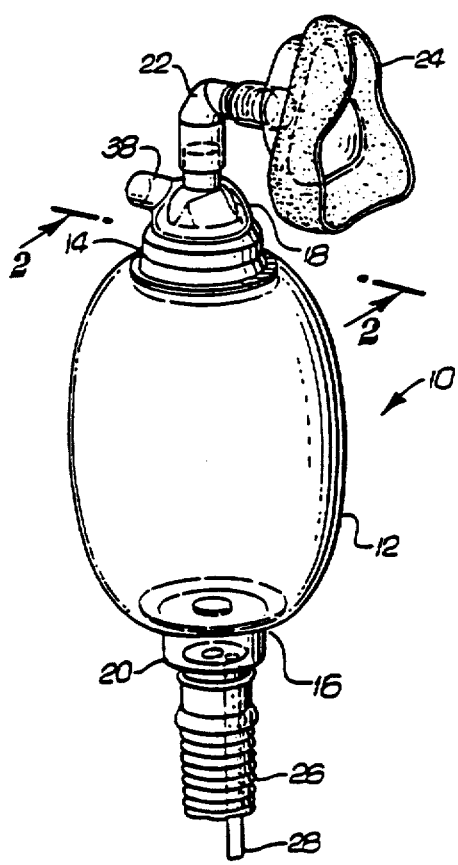
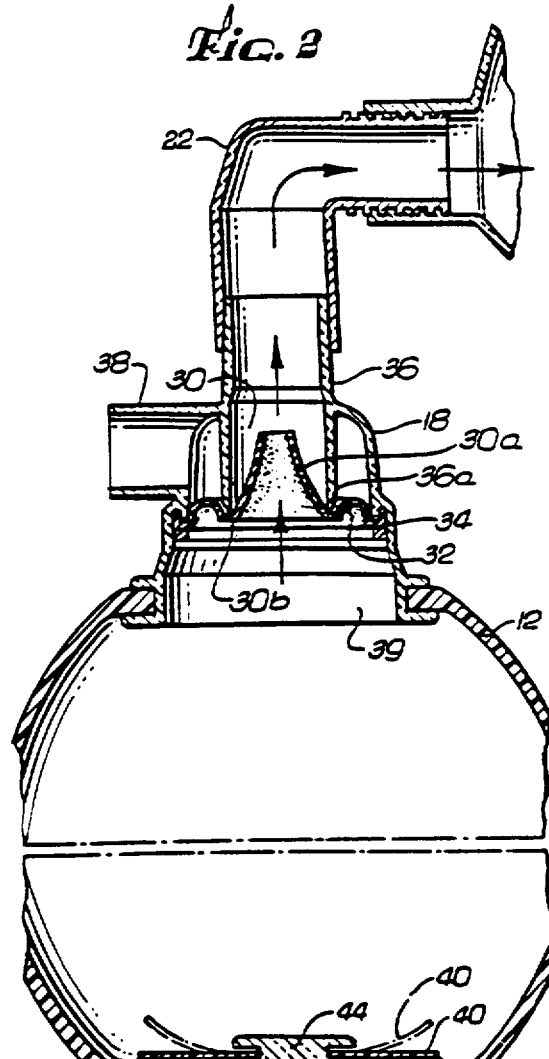
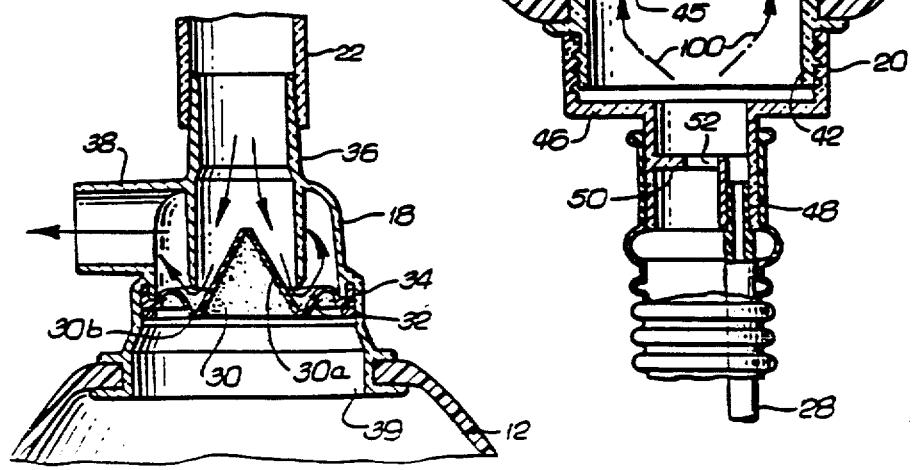

I claim:

1. A resuscitator comprising:
   (a) a flexible squeeze bag having a hollow interior and first and second openings at opposite ends thereof;
   (b) a directional control valve assembly fastened to said bag at said first opening;
   (c) a one-way gas inlet valve fastened to said bag at said second opening, said inlet valve permitting gas flow only into said hollow interior through said second opening;
   (d) said directional control valve assembly comprising a valve housing having a domed first end and a second end, said second end being secured to said bag around said first opening and having an open port formed therein which is coupled in flow communication with said hollow interior;
   (e) said assembly further comprising a tubular patient port joined to said first end of said valve housing and adapted to be coupled in gas flow communication to a patient, said patient port extending into said valve housing and including a tubular extension formed interiorly of said valve housing, and a unitary flexible duck-billed diaphragm valve;
   (f) said tubular extension being located substantially concentrically within said valve housing and terminating in a circular end, an annular exit passage being formed between said valve housing and said extension and an interior flow passage being formed within said extension, said interior flow passage being in flow communication with said first opening of said bag;
   (g) an unobstructed exit port formed in said valve housing in flow communication with said annular exit passage;
   (h) said duck-billed diaphragm valve including an outer peripheral portion, an inner duck-bill portion, a flexible annular portion connected to and surrounding said duck-bill portion, and a convolute shuttle portion connecting said peripheral and annular portions, said peripheral portion being secured to said valve housing, said annular portion being adjacent to and engageable with said circular end of said tubular extension, said duck-bill portion extending into said tubular extension, said shuttle portion extending into said annular exit passage, said shuttle portion, said annular portion and said duck-bill portion folding around said end and on opposite sides of said tubular extension; and
   (i) said unobstructed port and said annular exit passage forming a valveless exit flow path during exhalation and forming a valveless intake flow path during spontaneous inhalation when said second opening is occluded.

2. A resuscitator according to claim 1, wherein said unobstructed port is formed by a rigid cylindrical member attached to and extending substantially laterally outwardly from said valve housing.

3. A resuscitator according to claim 1, wherein said annular portion and said peripheral portion of said duck-bill diaphragm valve are substantially coplanar, and said shuttle portion extends arcuately into said annular exit passage and against said tubular extension.

4. A resuscitator comprising:
   (a) means for supplying gas having a hollow interior and first and second openings at opposite ends thereof;
   (b) a directional control valve assembly fastened to said gas supplying means at said first opening;
   (c) said directional control valve assembly comprising a valve housing having a domed first end and a second end, said second end being secured to said gas supplying means around said first opening and having an open port formed therein which is coupled in flow communication with said hollow interior;
   (d) said assembly further comprising a tubular patient port joined to said first end of said valve housing and adapted to be coupled in gas flow communication to a patient, said patient port extending into said valve housing and including a tubular extension formed interiorly of said valve housing, and a unitary flexible duck-billed diaphragm valve;
   (e) said tubular extension being located substantially concentrically within said valve housing and terminating in a circular end, an annular exit passage being formed between said valve housing and said extension and an interior flow passage being formed within said extension, said interior flow passage being in flow communication with said first opening;
   (f) an unobstructed exit port formed in said valve housing in flow communication with said annular exit passage;
   (g) said duck-billed diaphragm valve including an outer peripheral portion, and inner duck-bill portion, a flexible annular portion connected to and surrounding said duck-bill portion, and a convolute shuttle portion connecting said peripheral and annular portions, said peripheral portion being secured to said valve housing, said annular portion being adjacent to and engageable with said circular end of said tubular extension, said duck-bill portion extending into said tubular extension, said shuttle portion extending into said annular exit passage, said shuttle portion, said annular portion and said duck-bill portion folding around said end and on opposite sides of said tubular extension; and
   (h) said unobstructed port and said annular exit passage forming a valveless exit flow path during exhalation and forming a valveless intake flow path during spontaneous inhalation when said second opening is occluded.

5. A resuscitator according to claim 4, wherein said unobstructed port is formed by a rigid cylindrical member attached to and extending substantially laterally outwardly from said valve housing.

6. A resuscitator according to claim 4, wherein said annular portion and said peripheral portion of said duck-bill diaphragm valve are substantially coplanar, and said shuttle portion extends arcuately into said annular exit passage.

* * * * *

UNITED STATES PATENT AND TRADEMARK OFFICE
CERTIFICATE OF CORRECTION

PATENT NO.   :   4,774,941                         Page 1 of 3

DATED        :   October 4, 1988

INVENTOR(S)  :   Wallace F. Cook

It is certified that error appears in the above-identified patent and that said Letters Patent is hereby corrected as shown below:

The title page should be deleted to appear as per attached title page.

The sheet of drawings consisting of Figs. 1-3 should be replaced with the sheet of drawings attached hereto.

On the title page, "6 Claims," should read --6 Claims, 1 Drawing Sheet--.

Signed and Sealed this

Eighteenth Day of October, 1994

Attest:

BRUCE LEHMAN

Attesting Officer    Commissioner of Patents and Trademarks

United States Patent [19]

Cook

[11] Patent Number: 4,774,941
[45] Date of Patent: Oct. 4, 1988

[54] RESUSCITATOR BAG

[75] Inventor: Wallace F. Cook, Yorba Linda, Calif.

[73] Assignee: Intertech Resources Inc., Bannockburn, Ill.

[21] Appl. No.: 941,573

[22] Filed: Dec. 11, 1986

Related U.S. Application Data

[63] Continuation of Ser. No. 766,673, Aug. 16, 1985, abandoned, which is a continuation of Ser. No. 491,572, May 4, 1983, abandoned.

[51] Int. Cl.⁴ .................................................. A62B 7/04
[52] U.S. Cl. ............................... 128/205.13; 128/205.24; 137/102; 137/908
[58] Field of Search ............... 128/203.11, 203.28, 128/205.11, 205.13, 205.17, 205.24, 911; 137/102, 512.4, DIG. 9

[56] References Cited

U.S. PATENT DOCUMENTS

| Re. 24,193 | 8/1956 | Emerson | 128/205.24 |
|---|---|---|---|
| Re. 28,486 | 7/1975 | Ruben | 128/205.13 |
| 2,399,643 | 5/1946 | Kreiselman | 128/205.24 |
| 2,428,451 | 10/1947 | Emerson | 128/205.24 |
| 2,737,177 | 3/1956 | Anklin | 128/205.24 |
| 2,823,667 | 2/1958 | Raiche | 128/205.24 |
| 3,009,459 | 11/1961 | Ruben | 128/205.13 |
| 3,046,978 | 7/1962 | Lea | 128/205.13 |
| 3,086,542 | 4/1963 | Mosier | 137/102 |
| 3,093,153 | 6/1963 | Horowitz | 137/102 |
| 3,196,866 | 7/1965 | Adams | 128/205.24 |
| 3,262,446 | 7/1966 | Stoner | 128/205.13 |
| 3,356,100 | 12/1967 | Seeler | 128/205.13 |
| 3,363,833 | 1/1968 | Laerdal | 128/205.13 |
| 3,513,163 | 6/1970 | Freeman | 137/102 |
| 3,519,012 | 7/1970 | Van Patten | 137/102 |
| 3,556,122 | 4/1971 | Laerdal | 137/102 |
| 3,650,268 | 3/1972 | Ruben | 128/205.13 |
| 3,672,366 | 6/1972 | Barchell et al. | 137/102 |
| 3,726,274 | 4/1973 | Bird et al. | 128/205.12 |
| 3,739,801 | 6/1973 | Rudolph | 137/102 |
| 3,795,257 | 3/1974 | Fabish et al. | 137/102 |
| 3,799,185 | 3/1974 | Milnes et al. | 137/102 |
| 3,882,860 | 5/1975 | Frimberger | 137/DIG. 9 |
| 3,902,516 | 9/1975 | Rudolph | 137/102 |
| 3,942,547 | 3/1976 | Pfitzne | 137/102 |
| 3,978,878 | 9/1976 | Rudolph | 137/102 |
| 4,037,595 | 7/1977 | Elam | 128/205.11 |
| 4,071,025 | 1/1978 | Kohnke | 128/205.13 |
| 4,077,404 | 3/1978 | Elam | 128/205.13 |
| 4,084,606 | 4/1978 | Mittleman | 137/102 |
| 4,088,131 | 5/1978 | Elam et al. | 128/205.13 |
| 4,121,580 | 10/1978 | Fabish | 128/205.13 |
| 4,167,184 | 9/1979 | Kohnke | 128/205.13 |
| 4,190,045 | 2/1980 | Bartels | 128/205.24 |
| 4,239,038 | 12/1980 | Holmes | 128/205.13 |
| 4,374,521 | 2/1983 | Nelson et al. | 128/205.13 |
| 4,622,964 | 11/1986 | Flynn | 128/205.24 |

FOREIGN PATENT DOCUMENTS

| 745432 | 11/1966 | Canada | 128/205.24 |
|---|---|---|---|
| 0139363 | 5/1985 | European Pat. Off. | 128/205.13 |
| 2320118 | 4/1977 | France | 128/205.24 |
| 56058 | 5/1967 | German Democratic Rep. | 128/205.24 |
| 185702 | 8/1966 | U.S.S.R. | 128/205.24 |
| 748363 | 5/1956 | United Kingdom | 137/102 |
| 750152 | 6/1956 | United Kingdom | 137/102 |
| 791005 | 2/1958 | United Kingdom | 137/102 |
| 802217 | 10/1958 | United Kingdom | 137/102 |
| 843586 | 8/1960 | United Kingdom | 128/205.13 |
| 873790 | 8/1961 | United Kingdom | 128/205.24 |
| 1006984 | 10/1965 | United Kingdom | 128/205.13 |
| 1481246 | 7/1977 | United Kingdom | 137/102 |
| 2015349 | 9/1979 | United Kingdom | 128/205.13 |

OTHER PUBLICATIONS

AGA Medical, "AGA Revivator", 6 pages, (date unknown).
Steven P., McPherson, "Respiratory Therapy Equipment", (C. V. Mosely Co. St. Louis, 1977) pp. 141–157.
Puritan Medical Products, "PMR 2 Puritan Manual Resuscitator", 1980, pp. 1–8.
Laerdal Medical Corporation, "Laerdal Resuscitators", 2 pages (date unknown).
Narco Air Shields, "MS-30", 1 page, 1980.

Primary Examiner—Edward M. Coven
Assistant Examiner—K. M. Reichle
Attorney, Agent, or Firm—Marshall, O'Toole, Gerstein, Murray & Bicknell

[57] ABSTRACT

A resuscitation apparatus for use during medical procedures is disclosed. The device comprises a squeeze bag having a gas inlet and a gas outlet, and a specifically configured valve joined to the bag over the gas outlet. The valve housing includes a squeeze bag port in flow communication with the gas outlet opening, a patient port and an exhalation port. The valve disposed in the housing includes a portion for directing fluid from the squeeze bag through the patient port during inhalation or forced respiration and through the exhalation port during exhalation. Another portion of the valve closes off the exhalation port during inhalation or forced respiration such that fluid from the squeeze bag is directed to the patient.

6 Claims, 1 Drawing Sheet